(12) United States Patent
Johnson et al.

(10) Patent No.: US 6,790,298 B2
(45) Date of Patent: Sep. 14, 2004

(54) METHOD OF FABRICATION OF FREE STANDING SHAPE MEMORY ALLOY THIN FILM

(75) Inventors: A. David Johnson, San Leandro, CA (US); Vikas Galhotra, Union City, CA (US); Vikas Gupta, San Leandro, CA (US)

(73) Assignee: TiNi Alloy Company, San Leandro, CA (US)

( * ) Notice: Subject to any disclaimer, the term of this patent is extended or adjusted under 35 U.S.C. 154(b) by 0 days.

(21) Appl. No.: 09/902,856

(22) Filed: Jul. 10, 2001

(65) Prior Publication Data

US 2002/0046783 A1 Apr. 25, 2002

Related U.S. Application Data

(60) Provisional application No. 60/217,664, filed on Jul. 10, 2002.

(51) Int. Cl.[7] .............................................. C22C 45/00
(52) U.S. Cl. ...................................... 148/561; 148/563
(58) Field of Search ................................ 148/561, 563, 148/402, 403

(56) References Cited

U.S. PATENT DOCUMENTS

| | | | | |
|---|---|---|---|---|
| 4,864,824 A | * | 9/1989 | Gabriel et al. ................. | 60/527 |
| 5,061,914 A | * | 10/1991 | Busch et al. ................. | 337/140 |
| 5,722,989 A | * | 3/1998 | Fitch et al. ................. | 606/205 |
| 5,819,749 A | * | 10/1998 | Lee et al. ................... | 128/899 |
| 5,903,099 A | * | 5/1999 | Johnson et al. ................ | 216/2 |
| 6,592,724 B1 | * | 7/2003 | Rasmussen et al. ... | 204/192.15 |
| 6,605,111 B2 | * | 8/2003 | Bose et al. ................. | 623/1.18 |

FOREIGN PATENT DOCUMENTS

| | | | |
|---|---|---|---|
| JP | 07/90624 | * | 4/1995 |
| JP | 10/173306 | * | 6/1998 |

* cited by examiner

*Primary Examiner*—George Wyszomierski
(74) *Attorney, Agent, or Firm*—Richard E. Backus

(57) ABSTRACT

Methods of fabricating a free standing thin film of shape memory alloy material, and products made by the methods. A sacrificial layer of a metallic material is deposited onto the surface of a substrate. Then an amorphous shape memory alloy is sputter deposited onto the outer surface of the sacrificial layer. The sacrificial layer is etched away, leaving the thin film free standing, that is separated from the substrate. The thin film is annealed by heating into a crystalline state, with the annealing step carried out either after the film has been separated from the substrate, or while remaining attached to it.

7 Claims, 2 Drawing Sheets

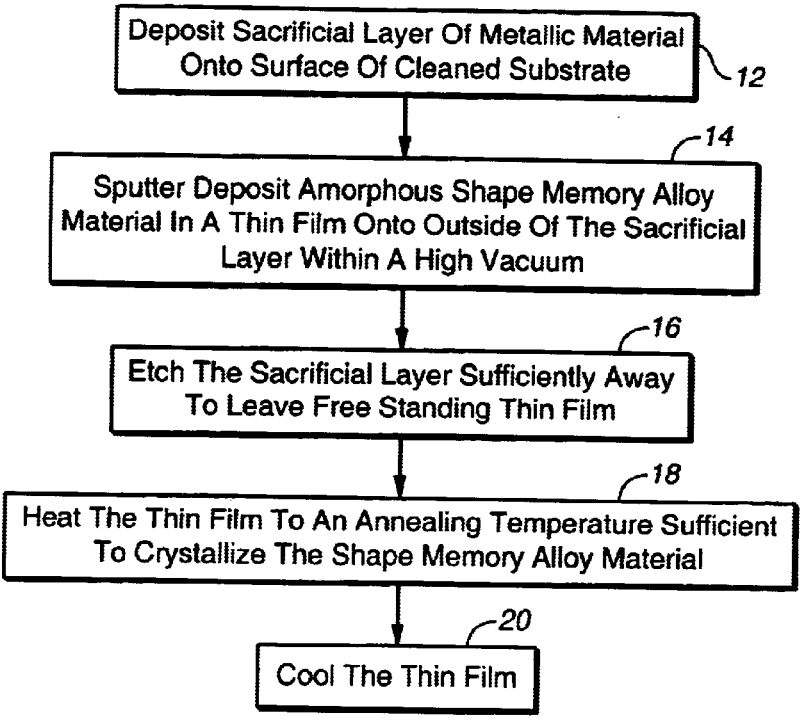
FIG._1
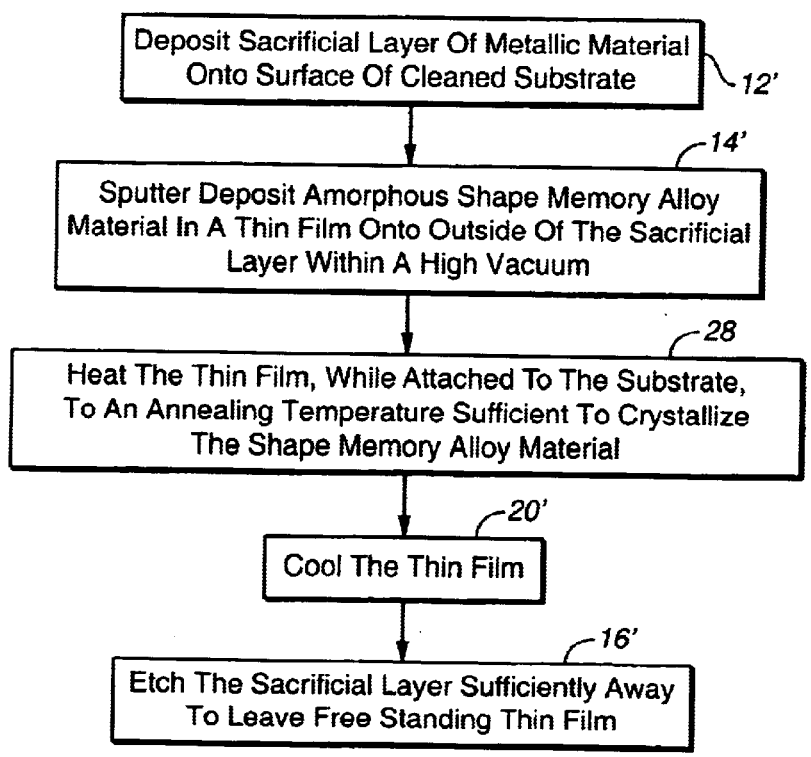
FIG._2

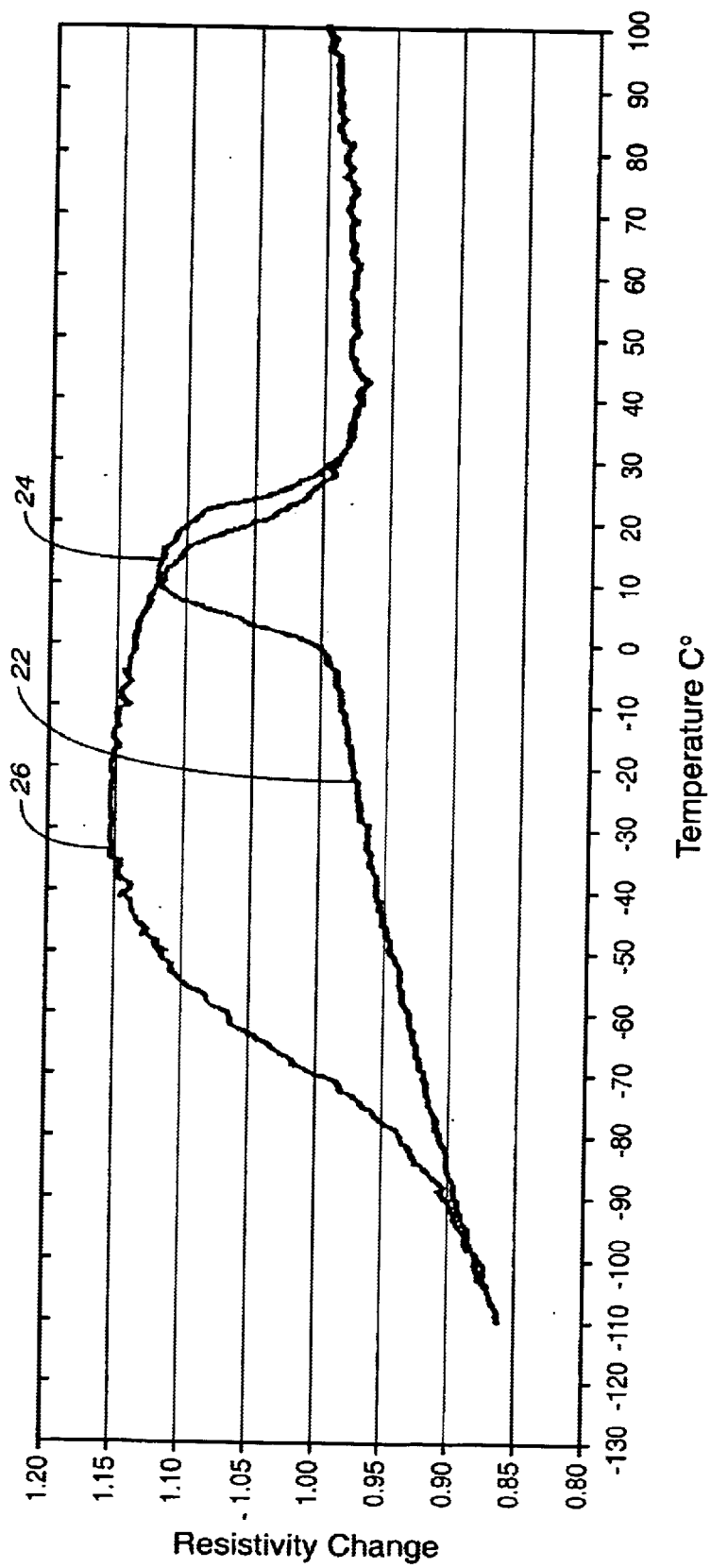
FIG._3

METHOD OF FABRICATION OF FREE STANDING SHAPE MEMORY ALLOY THIN FILM

CROSS REFERENCE TO PRIOR APPLICATION

This application claims the benefit under 35 USC §119(e) of U.S. Provisional application Ser. No. 60/217,664 filed Jul. 10, 2000.

BACKGROUND OF THE INVENTION

1. Field of the Invention

This invention relates in general to shape memory alloys (also called SMA), and more particularly to the fabrication of shape memory alloys in thin film form.

2. Description of the Related Art

Stainless steel remains the material of choice for many fields of medical devices implanted in the human body. For example, stents made of stainless steel are used to prevent restenosis after balloon angioplasty. Titanium-nickel alloy (TiNi), which when annealed so that it crystallizes possesses shape memory properties, has also come into increasing use for stents and other applications. To date, TiNi has been primarily used in tube or sheet form.

Various methods exist to draw tube or roll sheets of shape memory alloys like TiNi. These methods cannot guarantee the perfectly smooth surface finish required for various types of biomedical implants, especially those that will have contact with blood flow. A surface imperfection on a device like a stent can cause an embolism.

In addition to the problem of surface imperfections, material produced by drawing, hot rolling, or cold working techniques cannot match sputter-deposited materials for minimum possible thickness. Nor can such techniques be used to fabricate devices small enough for certain applications. There is a growing impetus for smaller and smoother stents that can be used in very small blood vessels such as those found in the brain to treat aneurisms or filter out blood clots.

Sputter deposited thin film shape memory alloys such as thin film comprised of TiNi overcomes these problems. Such films can be fabricated in a range of thickness from less than 1 $\mu$m to 40 $\mu$m. SMA material can be made in thin film configurations in accordance the teachings of U.S. Pat. No. 5,061,880 to A. David Johnson et. al., the disclosure of which is incorporated by this reference.

As is well known, an SMA material that has been annealed into a crystalline state undergoes a crystalline phase transformation from martensite to austenite when heated through the material's phase change transformation temperature. When below that temperature the material can be plastically deformed from a "memory shape" responsive to stress. When the SMA material is heated through the transformation temperature, it forcefully reverts to its memory shape while exerting considerable force.

OBJECTS AND SUMMARY OF THE INVENTION

It is a general object of the invention to provide methods for fabricating shape memory alloys into free standing thin films.

Another object is to provide free standing thin film structures made by such methods.

Another object is to provide methods for fabricating an SMA thin film that is biocompatible, free standing, smooth and uniform in thickness, thereby making it suitable for many medical devices and other applications.

BRIEF DESCRIPTION OF THE DRAWINGS

FIG. 1 is a flow chart showing the general method of fabricating a shape memory alloy free standing thin film in accordance with one embodiment of the invention.

FIG. 2 is a flow chart showing the general fabrication method in accordance with another embodiment.

FIG. 3 is a graph showing resistivity curves for a typical free standing shape memory alloy thin film fabricated in accordance with the methods of the invention.

DESCRIPTION OF PREFERRED EMBODIMENTS

In the drawings, FIG. 1 illustrates generally at 10 the general method steps in accordance with one preferred embodiment for fabricating a free standing SMA thin film structure. While the methods will be described for making the thin film of TiNi alloy material, the invention contemplates the use of other SMA materials for the thin films, such as TiNi—Cu, TiNi—Cr and TiNi—Hf alloys.

A substrate is provided with a cleaned and polished top surface. Preferably the substrate comprises a wafer of silicon, or a glass or pyrex slide, or a wafer of ceramic material. The size of the substrate wafer is not critical, and can vary from the smallest available substrate to the largest available substrate that can go through the various fabrication process machines. A typical circular substrate wafer size is 4" diameter.

The substrate is cleaned thoroughly in RCA cleaning solution (a mixture of ammonium hydroxide, hydrogen peroxide and DI water in the ratio of 1:1:5 respectively) at 80° C. for 30 minutes to remove any impurities such as grease and dust particles. Alternatively, other cleaning solutions can be used, such as Micro-90 (a commercially available mixture of salts of sodium, ammonium and acids).

In step 12, a sacrificial layer is formed that is comprised of a suitable metal which is compatible with the process, that is the metal can be etched without damaging the SMA thin film which will be sputter deposited in step 14. Chromium, aluminum or other such compatible metals can be used for this purpose. In this step the substrate wafer is placed in a chamber which is evacuated to a vacuum of $10^{-7}$ torr base pressure. The metal is heated and evaporated so that it deposits on flat top surface of the substrate in a layer of less than 1 $\mu$m thick.

In step 14, the SMA material is sputter deposited in a thin film onto the outside surface of the sacrificial layer. The substrate wafer as prepared in the manner described above is placed in a sputtering machine at $10^{-7}$ torr base pressure. The SMA material in amorphous form is sputtered at 2 millitorr argon pressure using a single TiNi DC magnetron target, and a DC power supply. High vacuum $10^{-7}$ torr base pressure helps in reducing the amount of oxygen that can be potentially absorbed by the titanium atoms. The film is deposited in amorphous form at the desired thickness, which can be in the range of ~1 $\mu$m to ~40 $\mu$m.

Alternatively, both the metallic sacrificial layer and the SMA film can be successively sputter deposited in the same machine without breaking the vacuum.

In step 16, the sacrificial layer is etched sufficiently away from the SMA film so that the film is free standing, meaning that the film is physically separated from the substrate. In this step a chemical etch solution is applied so that it begins to etch the sacrificial layer from the edges of the sputter deposited film with the etchant slowly proceeding inwardly and underneath the film. Because of the long etching time required to obtain free standing TiNi thin film having a large surface area, the sacrificial layer etchant should be selected so that it will not damage the SMA film during the etching step.

If chromium is used as the sacrificial layer, then the selected etchant can be a commercially available solution of ceric ammonium nitrate and nitric. Etching takes place at a temperature of approximately 25° C. (i.e. room temperature) for a period of approximately 24 hours for removing a 4" diameter film. To get an even larger area free standing thin films of SMA, longer etching times would be necessary. If aluminum is used as the sacrificial layer, an etchant solution of dilute Micro-90 can be used. Alternatively, a dilute sodium hydroxide solution or chrome etch can be used.

In step 18, the thin film is annealed at a temperature sufficient to crystallize the SMA material. The annealing step takes place in a high vacuum chamber (pressure <$10^{-5}$ torr) by heating on a hot plate or by using infrared heating at a temperature of 500° C. Annealing crystallizes the amorphous film, giving it the shape memory property.

In step 20, the thin film is allowed to cool to room temperature in the vacuum chamber. The thin film can then be used in its intended application.

The transformation temperatures of TiNi and other SMA thin film materials can be altered by varying the chemical composition of the material and the temperature at which they are annealed.

FIG. 2 shows another embodiment of the method by which, in step 28, the sputter deposited SMA thin film is annealed with the film still attached to the substrate, provided the sacrificial layer between the film and substrate will not diffuse into the SMA film. Chromium as the sacrificial layer satisfies this criterion. Once annealing is competed, the thin film is cooled at step 20'. Then in step 16' the sacrificial layer is etched away by a suitable chrome etchant to obtain a free standing thin film structure.

The described fabrication methods can be used to make three-dimensional films in cylindrical or conical shapes. Further, thin films produced by these methods can be lithographically patterned by the use of a mask and suitable etchant.

FIG. 3 is a graph show resistivity curves for free standing TiNi thin film fabricated by the method of FIG. 1. The graph plots resistivity change in the thin film as a function of temperature. The curves show the hysteresis and phase change associated with shape memory effect. Curve 22 shows resistivity change during the heating step with bulge 24 resulting from the crystalline phase change. Curve 26 shows resistivity change during the cooling step. These curves demonstrate that the thin film retains its shape memory property and is not damaged during the sacrificial layer etch step.

While the foregoing embodiments are at present considered to be preferred, it is understood that numerous variations and modifications may be made therein by those skilled in the art and it is intended that the invention includes all such variations and modifications that fall within the true spirit and scope of the invention as set forth in the appended claims.

What is claimed is:

1. A method of fabricating a shape memory alloy into a free standing thin film structure comprising the steps of placing within a vacuum a cleaned substrate, depositing a sacrificial layer on the substrate, sputtering an amorphous shape memory alloy and depositing the sputtered alloy in a thin film onto the sacrificial layer, applying a chemical etchant to the sacrificial layer for a time which is sufficient to etch the layer away to leave the thin film in a structure which is free standing from the substrate, heating the thin film to an annealing temperature which is sufficient to crystallize the shape memory alloy, and cooling the free standing thin film.

2. A method as in claim 1 and further characterized in that the step of depositing the sacrificial layer comprises depositing a material which can be removed by an etching process that does not cause damage to the amorphous shape memory alloy.

3. A method as in claim 2 and further characterized in that the material is selected from the group consisting of chromium and aluminum.

4. A method as in claim 1 and further characterized in that the sputtered alloy is deposited in a thin film having a thickness in the range of ~1 $\mu$m to ~40 $\mu$m.

5. A method as in claim 1 and further characterized in that the step of annealing by heating is carried out while the the thin film remains deposited onto the sacrificial layer.

6. A method of fabricating a shape memory alloy into a free standing thin film structure comprising the steps of placing within a vacuum a cleaned substrate, depositing a sacrificial layer on the substrate, sputtering an amorphous shape memory alloy and depositing the sputtered alloy in a thin film onto the sacrificial layer, heating the thin film to an annealing temperature while the the thin film remains deposited on the sacrificial layer, the annealing temperature being sufficient to crystallize the shape memory alloy, and applying a chemical etchant to the sacrificial layer for a time which is sufficient to etch the layer away to leave the thin film in a structure which is free standing from the substrate.

7. A method as in claim 6 and further comprising the step of cooling the free standing thin film.

* * * * *